(12) United States Patent
Kauvar

(10) Patent No.: US 7,060,447 B2
(45) Date of Patent: Jun. 13, 2006

(54) PROTEIN LOCALIZATION ASSAYS FOR TOXICITY AND ANTIDOTES THERETO

(75) Inventor: Lawrence M. Kauvar, Mountain View, CA (US)

(73) Assignee: Trellis Bioscience, Inc., San Francisco, CA (US)

( * ) Notice: Subject to any disclaimer, the term of this patent is extended or adjusted under 35 U.S.C. 154(b) by 0 days.

(21) Appl. No.: 10/713,234

(22) Filed: Nov. 13, 2003

(65) Prior Publication Data

US 2004/0110237 A1    Jun. 10, 2004

Related U.S. Application Data

(62) Division of application No. 09/332,611, filed on Jun. 14, 1999, now Pat. No. 6,673,554.

(51) Int. Cl.
*G01N 33/53*    (2006.01)
(52) U.S. Cl. .............................. 435/7.1; 435/6; 435/7.2; 435/7.8; 436/35; 436/63
(58) Field of Classification Search .................. 435/6, 435/7.1–7.8, 15, 23; 436/35, 63; 424/9.2; 356/345, 346; 364/496
See application file for complete search history.

(56) References Cited

U.S. PATENT DOCUMENTS

| | | | |
|---|---|---|---|
| 5,569,588 A | 10/1996 | Ashby et al. | 435/6 |
| 5,736,330 A | 4/1998 | Fulton | 435/6 |
| 5,777,888 A | 7/1998 | Rine et al. | 364/496 |
| 5,783,405 A | 7/1998 | Mochly-Rosen et al. | 435/15 |
| 5,784,162 A | 7/1998 | Cabib et al. | 356/456 |
| 5,811,231 A | 9/1998 | Farr et al. | 435/6 |
| 5,935,803 A | 8/1999 | Vasquez et al. | 435/15 |
| 6,054,286 A | 4/2000 | Villar et al. | 435/15 |
| 6,485,925 B1 | 11/2002 | Duesbery et al. | 435/23 |

FOREIGN PATENT DOCUMENTS

| WO | WO 97/14028 | 4/1997 |
|---|---|---|
| WO | WO 98/45704 | 10/1998 |

OTHER PUBLICATIONS

Ping et al, Isoform-selective activation of protein kinase C by nitric oxide in the heart of conscious rabbits: a signaling mechanism for both nitric oxide-induced and ischemia-induced preconditioning, Mar. 1999, Circ Res, 84, 587-604.*

Brick-Ghannam et al, Protein Kinase C (PKC) activation via Human Leucocyte Antigen Class II Molecules, 1991, 266:35, 24169-24175.*

Ping et al, Ischemic preconditioning induces selective translocation of protein kinase C isoforms and in the heart of conscious rabbits without subcellular redistribution of total protein kinase C activity, 1997, Circ Res, 81, 404-414.*

Gasman et al, Identification of a potential effector pathway for the trimeric Go protein associated with secretory granules, 1998, J Bio Chem, 273(27), p. 16913-16920.*

Hayashida et al, Intracellular third loop domain of angiotensin II type 2 receptor: role in mediating signal transduction and cellular function, 1996, J Bio Chem, 271(36), 21985-21992.*

Carayon et al, Involvement of peripheral benzodiazepine receptors in the protection of hematopoietic cells against oxygen radical damage, 1996, Blood, vol. 87 (7), 3170-3178.*

Kroemer et al, The mitochondrial death/life regulator in apoptosis and necrosis, 1998, Annu Rev Physio, 60:619-42.*

Benassi, L. et al. "In Vitro Testing of Tensides Employing Monolayer Cultures: A Comparison with Results of Patch Tests on Human Volunteers" Contact Dermititis 40:38-44 (1999).

Berridge, M.J. "Lymphocyte Activation in Health and Disease" Crit. Rev. Immunol. 17:155-178 (1997).

Beuers et al. "Modulation of Protein Kinase C by Tauolithocholic Acid in Isolated Rat Hepatocytes" Hepatology 29(2):477-482 (1999) Abstract.

Binquet, C. et al. "Principaux Logiciels Statistiques Utilisables en Epidemiologie" Rev. Epidemiol. Santé Publique 46:329-336 (1998) Abstract.

Cook, J.R. et al. "A Double-Label Technique that Monitors Sulfur Mustard Damage to Nuclei and Mitochondria of Normal Human Epidermal . . . " Toxicologic Pathology 25:481-486 (1997).

Curren, R. et al. "13th Meeting of the Scientific Group on Methadologies for the Safety Evaluations of Chemicals . . . " Environmental Health Perspect. 106(Suppl. 2):419-425 (1998).

Disatnik, M. et al. "Distinct Responses of Protein Kinase C Isozymes to c-erbB-2 Activation in SKBR-3 Human Breast Carcinoma Cells" Cell Growth and Differentiation 5(8):873-880 (1994).

(Continued)

*Primary Examiner*—Long V. Le
*Assistant Examiner*—Nelson Yang
(74) *Attorney, Agent, or Firm*—Morrison & Foerster LLP

(57) ABSTRACT

Intracellular translocation of proteins, particularly protein kinase C (PKC) isoenzymes, provides a surrogate test system for determining toxicity of candidate compounds. The profile of translocation with respect to at least one and preferably two or more signal transduction proteins can be correlated with that of known toxins. In addition, databases of such profiles with respect to toxins of various types provide a useful set of standards for evaluating toxicity of candidate compounds. Moreover, to the extent that a toxin's profile mimics that found in a diseased state, the toxin can be used to construct screens for compounds alleviating the disease.

13 Claims, No Drawings

OTHER PUBLICATIONS

Disatnik, M. et al. "Localization of Protein Kinase C Isozymes to c-erbB-2 Activation in SKBR-3 Human Breast . . . " Cell Growth Diff 5:873-880 (1994).

Duleba, A.J. et al. "Regression Analysis and Multivariate Analysis" Seminars in Reproductive Endocrinology 14:139-153 (1996).

Gygi, S.P. et al. "Correlation Between Protein and mRNA Abundance in Yeast" Molecular Cellular Biology 19:1720-1730 (1999).

Kiley, S. et al. "Differential Localization of Protein Kinase C Isozymes in U937 Cells: Evidence for Distinct Isozyme Functions During Monocyte Differentiation" Journal of Cell Science 108(3):1003-1016 (1995).

Kosaka et al. "Differential Localization and Expression of Alpha and Beta Isoenzymes of Protein Kinase C" Journal of Neuroscience Research 54(5):655-663 (1998) Abstract.

Kressel, M. et al. "Distinction of Apoptotic and Necrotic Cell Death by In Situ Labeling of Fragmented DNA" Cell Tissue Research 278:549-556 (1994).

LeClaire, J. et al. "Industry Experience with Alternative Methods" Toxicol Letters 102-103:575-579 (1998).

Liedtke, C.M. et al. "Antisense Oligonucleotide to PKC Alters cAMP-Dependent Stimulation of CFTR in Calu-3 Cells" Am. J. Physiol. 275:C1357-64 (1998).

Mochly-Rosen, D. "Localization of Protein Kinases by Anchoring Proteins:A Theme in Signal Transduction" Science 268:247-251 (1995).

Mochly-Rosen, D. et al. "Modulating Protein Kinase C Signal Transduction" Advances in Pharmacology 44:91-145 (1998).

Oancea, E. et al. "Green Fluorescent Protein (GFP) Tagged Cysteine-Rich Domains from Protein Kinase C as Fluorescent Indicators . . . " J Cell Biol. 140:485-498 (1998).

Rabinowitz, J.D. et al. "Kinetic Discrimination in T-Cell Activation" Proc. Natl. Acad. Sci. USA 93:1401-1405 (1996).

Smith, C.N. et al. "Presence of Methenamine/Glutathione Mixtures Reduces the Cytotoxic Effect of Sulphur Mustard on Cultured . . . " Human & Experimental Toxicology 16:247-253 (1997).

Yazlovitskaya, E. et al. "Selective Farnesol Toxicity and Translocation of Protein Kinase C in Neoplastic HeLa-S3K and Non-Neoplastic CF-3 Cells" Cancer Letters 88(2):179-183 (1995).

Zhou, L.Y. et al. "Differential Activation of Protein Kinase C Isozymes by Phorbol Ester and Collagen in Human Skin . . . " J Investigative Dermatology 107:248-252 (1995).

* cited by examiner

PROTEIN LOCALIZATION ASSAYS FOR TOXICITY AND ANTIDOTES THERETO

CROSS-REFERENCE TO RELATED APPLICATION

This application is a divisional of U.S. Ser. No. 09/332,611 filed 14 Jun. 1999 and now U.S. Pat No. 6,673,554. The contents of that document is incorporated herein by reference.

TECHNICAL FIELD

The invention relates to methods to evaluate toxicity of pharmaceuticals or other compounds intended for human or animal use. In particular, it concerns evaluating the toxicity of candidate compounds by assessing the effect of these compounds on localization of signal transduction proteins, particularly the protein kinase C (PKC) isoenzymes. Such assays can then be used to identify antidotes. To the extent that a disease state can be mimicked by a toxin, the invention further provides an assay for drug discovery.

BACKGROUND ART

The value of recognizing the toxicity of compounds intended as pharmaceuticals, cosmetics, foods, or other applications where the compounds come into contact with humans or other animals is evident. Because of ethical considerations, not to mention economic ones, of using animal models to predict toxicity against humans, a number of surrogate toxicity tests have been developed permitting more efficient and less controversial approaches to evaluating the capacity of compounds to impact the viability or well being of organisms. For example, a human keratinocyte cell line (SVK-14) has been validated as a model for the effects of mustard vesicants on basal epidermal keratinocytes (Smith, C. N., et al., *Human Exp Toxicol* (1997) 16:247–253). Normal human epidermal keratinocytes in vitro have also been used to monitor sulfur mustard damage to nuclei and mitochondria (Cook, J. R., et al., *Toxicol Pathol* (1997) 25:481–486). Apoptosis and necrotic cell death have also been studied as a result of contact with toxic compounds (Kressel, M., et al., *Cell Tissue Res* (1994) 278:549–556).

The cosmetics industry has been particularly concerned with substituting in vitro tests for in vivo evaluations of toxins. LeClaire, J. et al. *Toxicol Lett* (1998) 102–103:575–579 describes the experience of L'Oreal in substituting an in vitro system whereby Langerhans cells are introduced into reconstructed epidermis as an alternative test for skin sensitization. The article states that L'Oreal was able totally to ban animal testing on cosmetic products. However, Benassi, L. et al. *Contact Dermatitis* (1999) 40:38–44 describes a similar attempt to provide a model for whole animal testing. The validity of a monolayer culture system of human keratinocytes was used as a surrogate for in vivo acute skin irritancy tests for several compounds. The results did not entirely correlate, and the authors conclude that this suggests that the keratinocyte monolayer cell culture technique cannot directly replace in vivo methods. Further, Curren, R. et al. in an abstract published in *Environ Health Perspect* (1998) 106 (Suppl. 2):419–425 reviews the current state of in vitro testing and concludes that in order to progress in the areas of eye and skin irritation, it is necessary to expand knowledge of toxic markers in humans and the biochemical basis of irritation. Thus, attempts to replace in vivo testing with in vitro models have not been entirely successful.

Other approaches will be familiar to the practitioner. Gene expression profiles obtained in response to treating cells or tissues with toxins or other compounds are commonly used as indices of the effects of these compounds. Gene expression can be evaluated either by assessing the pattern of distribution of various mRNAs or by looking directly at the protein levels or activities that result. U.S. Pat. No. 5,811,231 (Xenometrix) discloses a surrogate marker comprising detection of gene transcription from any of several disclosed "stress response" promoters. It is desirable to create surrogates for other kinds of toxicity, such as hypertension, for example, which requires correlating molecular and physiological phenotypes. One such surrogate is disclosed in U.S. Pat. No. 5,569,588 (Acacia) which discloses methods for drug screening by providing a plurality of separately isolated cells, each having an expression system with a different transcriptional regulatory element. Contacting this plurality of cells with a drug candidate and detecting reporter gene product signals from each cell provides a profile of response to the drug with regard to this multiplicity of regulatory elements. In addition, U.S. Pat. No. 5,777,888 (Acacia) describes a system for generating and analyzing a stimulus response output from a collection of signals. The description includes artificial intelligence systems such as expert systems and neural networks for this purpose. These methods, however, rely on gene transcription which is a downstream effect from protein localization as provided hereinbelow.

Since mRNA abundance is now known to be poorly correlated with protein abundance in many instances (Gygi, S. P., et al. *Mol Cell Biol* (1999) 19:1720–1730 which is incorporated herein by reference), direct examination of the proteins is useful. Standard methods to analyze thousands of proteins in parallel, typically using 2-D gels and mass spectroscopy, are complicated by the frequent occurrence of post-translational modifications. Since the functional impact of many of these modifications is to change subcellular localization, direct visualization of protein location simplifies the analysis. Since degradation can be considered a translocation to the void compartment (typically, via the proteosome degradation machinery), abundance of the protein can be included in the same analysis. Thus, as used here, "intracellular localization" includes a determination of protein levels and changes therein.

Structure activity relationships of compounds having similar toxicities have also been used to predict the behavior of compounds of analogous structures. In addition, cell-based high throughput assays wherein a flow cytometer can be used to identify dead cells, especially after staining with a membrane-impermeable dye, can be used to assess a response. None of these methods is based on assessing intracellular localization.

It has previously been suggested to use multivariate statistical methods to analyze toxicity data obtained from a multiplicity of assays. The National Cancer Institute has assayed over 60,000 compounds for cytotoxicity against 60 cell lines, thus creating an oncology oriented database. Compounds with similar mechanisms of cellular destruction show strong correlations in their activity profiles across the panel. For example, microtubule disrupting agents are particularly effective in some of the cell lines and particularly ineffective on others. A candidate compound which shows a similar pattern has a high probability of exerting an effect on microtubules. This panel was also evaluated with respect to specific responses to the compounds, such as the expression of particular proteins, for example, p53. A cluster of proteins was identified whose expression is correlated with poor efficacy of alkylating agents, but not correlated with efficacy of antitubulin drugs. Thus, by testing a candidate against the 60 cell lines and evaluating the expression of this cluster of proteins, it would be possible to predict whether the compound would or would not be an effective alkylating agent.

Many toxicities encountered clinically affect only a small fraction of the population, but the undetectable effects on the remainder of the population are undoubtedly more widespread. Therefore, assays which assess damage below the clinical threshold and below the threshold detectable by gene transcription are desirable.

There remains a need to develop systems that can serve as accurate surrogates for predicting a wider range of potential toxicity of candidate compounds, assessing the nature of the mechanism by which they exert their toxic effects, and evaluating efficacy of treatment protocols. The present invention offers such a system.

DISCLOSURE OF THE INVENTION

The present invention uses the intracellular distribution of proteins which are involved in signal transduction as a surrogate for evaluating toxicity. By focusing on intracellular localization in response to test compounds, the present invention offers the ability to provide a large number of data points, essentially simultaneously, so that a toxicity "footprint" of a particular compound can be obtained. Similarly, the efficacy of antidotes to the toxin can be assessed by evaluating the changes in the footprint when a proposed therapeutic protocol is tested against the surrogate. It is also an aspect of the invention to compare the footprint associated with a defined toxin with the footprint associated with a disease state. Where similar footprints are found, the toxin-induced footprint can be used as a model for the disease state and therapeutic protocols for the disease state evaluated accordingly.

In a particularly preferred embodiment, the invention also takes advantage of the crucial role played by protein kinase C (PKC) isozymes in intracellular signaling. Because intracellular signaling is closely associated with both positive and negative metabolic effects, monitoring PKC activity provides an ideal basis for generating a broadly useable database of toxicity profiles. It is known that the PKC isozymes react to stimuli by altering their subcellular localization. The "before and after" locations are distinctive for each isozyme in each cell type. Thus, assessing the subcellular localization of the 11 PKC isozymes in response to contact by potentially toxic compounds serves to create a profile for the response to individual compounds. By correlating the profiles of a multiplicity of compounds with their toxic behavior, a database can be created so that testing an individual compound with respect to its effect on PKC isoenzyme intracellular localization can serve as a surrogate for evaluating not only whether or not it is toxic, but the nature of its toxicity.

As stated above, the footprint of the toxin even with respect to the limited population of PKC enzymes may correlate with the footprint associated with a disease. In this instance, therapeutic protocols for the disease, as well as possible antidotes for the toxin, can be evaluated by assessing their effects on the intracellular localization footprint.

Thus, in one aspect, the invention is directed to a method to evaluate the toxicity of a candidate compound, which method comprises observing the intracellular localization of at least one PKC isoenzyme or other signal transduction protein in the presence and the absence of the candidate compound; comparing the intracellular localization pattern in the presence of the candidate compound with the intracellular localization pattern of said signal transduction protein in the presence of a known toxin, whereby similarity of the pattern observed with respect to the candidate compound to that observed for said known toxin identifies said candidate compound as a toxic compound. It is also likely that the candidate compound has a similar mechanism of action when the similarity in pattern is observed using more than one signal transduction protein and/or more than one cell type, and/or by measuring translocation as a function of time to obtain the profiles or footprints.

In another aspect, the invention is directed to a method to obtain a database of signal transduction protein localization profiles in response to toxic compounds, and to the database thus obtained. Typically, an individual toxin will be evaluated with respect to its effect on at least one and preferably more than one protein. If several proteins are used in the evaluation, a profile for a single toxin can be obtained. Additional toxins will have similar or different profiles.

In another aspect, the invention is directed to a method to refine toxin footprints by expanding the protein panel under inspection, followed by identification of the principal factors most strongly correlated with a particular toxicity.

In still another aspect, the invention relates to a method to identify a treatment protocol for a disease condition which method comprises identifying a cellular function the inhibition of which would ameliorate said disease condition, identifying, by the method of the invention, a toxin which inhibits said cellular function, thus identifying said toxin as a medicament to ameliorate the condition.

In still another aspect, the invention is directed to a method to identify an antidote for a toxin by assessing the ability of a candidate antidote to reestablish the normal intracellular localization footprint that has been distorted by the toxin. In instances where a disease state is characterized by distortion of the normal footprint, therapeutic protocols for the disease state can similarly be evaluated.

MODES OF CARRYING OUT THE INVENTION

The invention methods rely on the ability of currently available wide-field microscopic techniques to assess the intracellular location of proteins, which can be labeled for observation as described below. Typically, proteins that vary their intracellular location in response to stimuli are "signal transduction proteins." Typical of such proteins are the protein kinase C (PKC) isoenzymes. However, other proteins involved in signal transduction are known and their roster continues to grow as the processes of the living cell continue to be elucidated.

This roster includes, for example, cell surface receptors which often aggregate in response to specific stimuli. It also includes adaptive proteins, for example proteins with an SH2 or SH3 domain. These typically translocate to activated receptors. Additional proteins are then recruited into such a complex, typically expressing an enzymatic function, for example, phospholipases or cyclic nucleotide synthases. Of course, transcription factors move from cytoplasm to the nucleus, for example, steroid receptors, STATS, NF-κB, AP-1 (fos-jun).

In addition, some proteins change organelle localization on damage to the organelle, for example cytochrome C leaks out of damaged mitochondria. Still other proteins traffic subcellularly, for example the cystic fibrosis chloride channel. About 5% of this channel per hour cycles from the cell surface into coated pits and thence into the cell interior. The GLUT-4 glucose transporter moves to the cell surface in response to signals generated initially by insulin binding to the receptor. Finally, the cytoskeleton and associated proteins change in a variety of ways, including an overall vectorial bias in orientation and in the position of the microtubule organizing center.

Such changes are illustrated below with respect to T-lymphocytes.

The toxicity of a particular compound may be assessed by the translocation of only a single signal transduction protein. However, even more useful is the pattern of intracellular translocations of a multiplicity of proteins caused by stimulation by a toxin or other probe or by an abnormality in the condition of the cell. This pattern of intracellular localization can be considered a profile or a "footprint" of the response to a stimulus, for example, a toxin, or as a result of a disease or other abnormal condition. Changes in this footprint in response to various additional stimuli, therefore, can be used to evaluate efficacy of treatments with regard to abnormal conditions or antidotes to toxins.

The known patterns of protein kinase C distribution can be used as an illustration. According to the method of the invention, the cellular response to a compound to be tested for toxicity is measured in terms of the localization of at least one PKC isoenzyme. There are 11 PKC isoenzymes known. It is known that these isoenzymes mediate different biological effects. For all isoenzymes, however, it is believed that the translocation of the PKC, often from the cell soluble fraction to the cell particulate fraction, is required for activity (Mochly-Rosen, D., *Science* (1995) 268:247–251). Indeed, isozyme-specific antibodies have been used to determine the subcellular localization and stimulation-induced translocation of several PKC enzymes in human breast cancer cell lines (Disatnik, M-H., et al., *Cell Growth Diff* (1994) 5:873–880; in cultured rat cardiac myocytes (Disatnik, M. H., et al., *Ex Cell Res* (1994) 210: 287–297; and in human dermal microvascular endothelial cells (hDMEC) (Zhou, L. Y., et al., *J Invest Dermatol* (1995) 107:248–252). For example, in hDMEC, after stimulation with the PKC agonist phorbol myristic acetate (PMA), the seven isoenzymes studied showed distinctive before/after localizations, as shown in Table 1.

TABLE 1

| PKC Isoenzyme | From | To |
|---|---|---|
| α | cytosol | perinuclear membrane |
| β | " | nucleus |
| βII | nucleus | filamentous structures |
| δ | cytosol | cytoskeletal elements |
| ε | periphery | perinucleus |
| ζ | fibrillar structures | no change |
| η | nucleus | no change |

It is apparent from these results that a useful profile of the cells' response to an individual compound can be created by observation of the translocation of PKC isoenzymes wherein the translocation profile may be partial or complete. Since such profiles can be correlated with toxic effects measured independently, the profile becomes a surrogate for assessing not only the toxicity of the compound per se, but the type of toxic response it will exhibit.

As used herein, with respect to the use of PKC isoenzymes as the substrate surrogates, the term "profile" or "footprint" for a particular compound refers to the pattern of translocation observed for a multiplicity of PKC isoenzymes and/or cell types and/or by measuring translocation as a function of time. While profiles are especially useful in identifying particular types of toxic activity, a simple mimic of a particular translocation for a single PKC in a single cell type, if properly validated, can be used as an index for toxicity, in the sense of a surrogate system for toxic activity per se.

For example, phorbol myristic acetate (PMA) binds to the C1 region on the regulatory domain of PKC. Oancea, E. et al. *J Cell Biol* (1998) 140:485–498 describes assaying this response by employing a fusion of the C1 region with green fluorescent protein (GFP). In response to PMA, this fusion protein moves from a diffuse cytoplasmic localization to a membrane bound one. Thus, the C1-GFP fusion can act as a reporter for the endogenous analog of PMA, which is diacyl glycerol (DAG). Similarly, the regulatory subunit of the cAMP-dependent kinase, PKA, dissociates from the catalytic subunit when cAMP levels rise, followed by translocalization of the catalytic subunit. A GFP fusion to the catalytic subunit would thus provide a reporter for cAMP. More broadly, any translocating domain can be linked to an observable protein, such as GFP, and act as a reporter for the translocation inducing signal. The observable aspects may also be inherent.

Similarly, as described above, additional signal transduction proteins can be labeled and their intracellular locations evaluated. The profile or footprint with respect to these proteins is defined similarly.

Means for assessing the intracellular localization of the signal transduction proteins are available in the art. This is, of course, apparent from the studies cited above. A preferred method for observation uses a commercially available wide-field deconvolution microscope marketed as the Delta Vision Microscope from Applied Precision (Seattle, Wash.). This is an illustrative instrument of a class of "wide-field" microscopes which utilize silicon chip charge-coupled device (CCD) technologies to convert light directly into digital signals. An improved form of this commercially available example is described in U.S. patent application Ser. No. 60/102,434 filed 3 Sep. 1998 and incorporated herein by reference.

Intracellular localization is typically performed using antibodies to the relevant protein. Many such antibodies are commercially available (Research and Diagnostic Antibodies, Berkeley, Calif.). The antibodies are attached to individual labels so that they can be distinguished. A particularly preferred approach to individually labeling reagents, such as these antibodies, is described in U.S. Ser. No. 09/146,984 filed 3 Sep. 1998 and incorporated herein by reference. Briefly, particulate "beads" used to label specific reagents such as the antibodies are provided in a multiplicity of hues by varying the ratios and amounts of individual fluorescent dyes coupled to the beads. By varying these amounts, a large number of different "hues" can be created thus distinguishing antibodies coupled to beads of different hues.

Other methods for measuring translocation are set forth in U.S. patent application Ser. No. 09/144,609 filed 31 Aug. 1998, incorporated herein by reference, and in the continuation-in-part application of U.S. patent application Ser. No. 09/146,984, also incorporated herein by reference, having attorney docket no. 38851-20101.20.

Methods for immunostaining the intracellular components and fixing the immunostained cells have been described by Zhou, L. Y., et al., *J Invest Dermatol* (1995) 107:248–252, cited above. Briefly, the cells are fixed in cold acetone, blocked with 1% normal growth serum for 1 hour prior to overnight treatment with isoenzyme-specific anti-PKC antibody. After washing, the specimens are prepared for microscopy by mounting in 90% glycerol in PBS with 0.1% azide and 3% diazabicyclo[2.2.2]octane (an anti-quenching compound). The time courses of responses ranging from minutes to hours are developed for each of the isoenzymes in response to the best compounds or the toxin standards. Relevant categories for intracellular location include nuclear, perinuclear, diffuse cytoplasmic, cytoplasmic fibril-associated, and membrane-associated.

In order to assess the toxicity of an individual compound, however, the profile of translocated signal transduction proteins obtained in response to that compound must be correlated with profiles obtained from compounds of known toxicity. There is, of course, a litany of compounds known to be toxic. Suitable toxic compounds useful to create the database with regard to skin irritancy include, for example, ifosfamide, a cancer therapeutic mustard; phorbol myristic acid (PMA), a known PKC agonist with skin irritant properties; urushiol, the irritant in poison ivy. For other kinds of toxicity, suitable reference compounds include the enterotoxins of *Staphylococci*; the exotoxins of the *Streptococci*, other bacterial toxins such as cholera toxin, anthrax toxin, and toxins derived from *E. coli, Salmonella, Shigella* and *Campylobacter*. The mechanisms of many of these toxins are known. For example, the enterotoxins and exotoxins of the *Staphylococci* and *Streptococci* respectively, provoke effects in the immune system mediated by cytokines secreted from stimulated T-cells; other toxins act by disrupting signal transduction components including ADP ribosylating proteins, adenyl and guanylate cyclases, calcium and protein kinases.

The effects of toxins in specific cell death assays has been cited above. In assessing the effect of mustards on nuclei, the membrane-permeable SYTO nuclear stain is used; effects on metabolism are determined by using the nontoxic dye for mitochondria, Alamar blue. In a useful assay for apoptosis, a fluorescent label is attached to 3' ends of fragmented DNA. Fragmented DNA distinguishes apoptosis from necrosis. In the early stages of apoptosis, DNA breaks are diffusely distributed in the entire nucleus except for the nucleolus with crescent-like accumulations beyond the nuclear membrane. In more advanced states, the nucleus is transformed into many round bodies with intense labeling. In necrosis, however, no DNA fragmentation occurs at the outset of cell death, only appearing 24 hours after cell death, long after the point when cell membrane integrity is lost.

Thus, by using suitable prior art assays, the nature of the toxic effects of individual toxins used to create the database can be assessed.

When profiles for a number of toxins have been obtained so as to provide a database, established pattern recognition techniques can be employed to rank order the signal transduction protein distributions or the timing thereof as predictors of apoptosis or other mechanisms of toxicity. Application of such techniques is aided by the fact that the microscope images are collected in digital form. These multivariate techniques are described, for example, in Duleba, A. J., et al., *Semin Reprod Endocrinol* (1996) 14:139–153;Binqet, C., et al., *Rev Epidemiol Santé Publique* (1998)46:329–336. Thus, the entire database can be stored and manipulated in computer-readable form. A typical correlation available by such manipulation of the database is, for example, a localization pattern that is a diagnostic marker for eventual apoptosis in basal epithelial cells. Such correlations are possible because different signal transduction proteins mediate different biological effects typically with a reinforcing effect. In this way, toxicity assays can be performed more quickly and easily. Antidote screening is further enabled by such an improvement in throughput.

A particularly useful aspect of multivariate analysis is "factor analysis," used to distinguish "driver" phenotypes from "passengers." The ideal marker for a particular toxin is always associated with the toxin and never observed in its absence. Most observed changes are passengers, responding to a driver phenotype. Since regulatory networks typically use balanced, opposing activities, the driver phenotype might, for example, be a concurrent increase in A with a decrease in B. The ratio of A:B represents the driver phenotype. In n dimensions, the driver phenotype can be more complex.

The ability to correlate a profile with a particular cellular effect is valuable on a macroscopic scale as well, since tissue pathology is a consequence of cellular responses. For example, both chemical and heat-induced skin burns share tissue level features although they are produced at different times after exposure. These features include erythema followed by subcutaneous edema which develops into blisters involving superficial layers of the skin which heal by scab formation. These features have been traced to separation of the basal layer from the overlying dermis to form small vesicles, which is caused by basal cell death. In the case of chemical burns, the dying cells show the hallmarks of apoptosis, including condensation of nuclear chromatin and perinuclear vacuolation.

Thus, by using a toxin-induced profile or footprint as a model for a preapoptotic state of basal cells, the effect of various therapeutic agents on the late stage tissue level disease can be predicted. Successful therapeutic agents will restore the footprint to that of a normal cell, or to one more closely resembling it.

The localization of any signal transduction protein may be used as an appropriate data point. However, the ubiquitous role of PKC in cellular signaling processes allows a wide range of toxicities to be monitored using just these proteins. More refined analysis (fewer false positives and more informative classification) is enabled by examination of larger numbers of proteins. That is, the perfect driver phenotype will include contributions by many individual proteins. If a particular PKC isozyme's contribution represents 30% of the statistical variance in that ideal driver phenotype, then just using PKC alone is suboptimal but still useful. Moreover, working forward instead of backward, PKC alone provides a benchmark for evaluation of other potential contributors to the driver phenotype—the new protein must increase the percent variance accounted for. With the multihue tag approach described above, many thousands of proteins can be monitored concurrently. Multivariate regression of translocation phenotypes versus toxicity will identify that cluster of coordinated responses that accounts for the largest percent of variance. This cluster, or more precisely the dominant contributors, are an approximation to the perfect driver phenotype. Novel compounds can then be classified by the degree of overlap of their effects with various such coordinated responses.

As a simplified illustration, a chart of localization patterns for two PKC isoenzymes might be shown as below, with crosses indicating the effect of five known skin irritants.

Code: N = nuclear; C = cytoplasmic; F = fibrillar elements; M = membrane

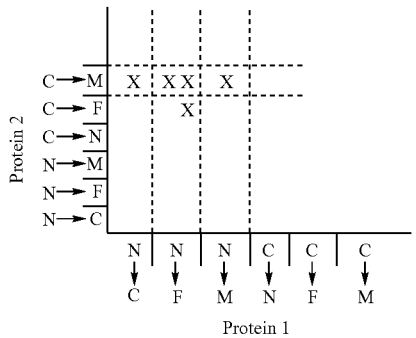

In this example, the combination of data from both proteins is a more reliable predictor than either alone. That is, the driver phenotype=40% protein 1 (N→F)+60% Protein 2 (C→M).

Clearly, the more data points that compose the profiles, the more valuable and predictive are the conclusions drawn from changes in the footprint. The possibilities are extremely large. Considering only the 11 PKC isoenzymes, each of which can be in one of five arbitrarily designated places before and after treatment with a stimulant (25 combinations) there are $25^{11}$ categories, for more than the number of known toxins. If additional signal transduction proteins are included, the numbers are much larger. Thus, multivariate statistics and systems such as neural nets and fuzzy logic become essential to deal with the volume of data in a search for approximates to the ideal driver.

It has become clear that nearly all diseases and chronic conditions involve damaged proteins. The damage may be directly inherited in the genome or later acquired in the genome by mutation or may be directly acquired at the protein level. Thus, toxins may be found at a protein level which alter the pattern of proteins to mimic or overcome the diseased state or condition. Generally, it is more facile and direct to regulate the level of a disease model by applying and withdrawing toxin than by turning genes on and off. In this way, subthreshold disease states can also be identified in a small population, allowing extrapolation to expected supra-threshold toxicity rates expected, assuming Gaussian distribution of modifier factors. Moreover, agents that shift the network from the disease pattern to the subthreshold pattern can be identified.

The invention method takes advantage of the homeostatic nature of the network system that controls cellular metabolism. Perturbation of the normal state by a toxin activates proteins initiating the maximally perturbed state, but also proteins which facilitate a decay back to the normal condition, for example, when toxin is withdrawn. Disease conditions which negatively affect one such set of proteins should be compensated by the identified agent.

Thus, in summary, the method of the invention provides a simple surrogate method to test compounds for toxic effect by simply observing the translocation or the translocation profile characteristic of toxicity in response to the compound. It further permits the nature of the toxic reaction to be assessed by comparing the profile to the database created from profiles of toxins whose mechanism of action is known. Finally, it permits identification of medicaments which are useful in effecting inhibition of target metabolic processes that may be associated with disease.

The following examples are to illustrate but not to limit the invention. The examples describe particular scenarios of protein localization useful in the invention.

EXAMPLE 1

T-Cell Activation

An inappropriately high level of T-cell activation underlies numerous diseases, including allergy, asthma, numerous autoimmune diseases such as type I diabetes and multiple sclerosis, and transplant rejection. Insufficient activation underlies vaccine failure and weakened defense against parasites and cancer. Both death of T-cells as well as diminished function underlies HIV induced immunodeficiency.

Numerous proteins change their subcellular localization when T-cells are stimulated, as follows:

(i) T-cell receptors (TCR) aggregate at the point of contact between the T-cell and antigen presenting cell (APC).

(ii) The activation TCR and associated protiens have tyrosine phosphorylation activity and the new phosphotyrosine motifs attract SH2 domain protiens such as phospholipase C, which generates second messengers including inositol phosphates and diacylglycerol (DAG). DAG is a protien kinase C (PKC) activator.

(iii) PKC-theta translocates to the clustered TCRs.

(iv) Actin Cytoskeleton rearranges, with the associated protien talin becoming concentrated at the zone of TCR clustering.

(v) The G-coupling protien ras translocates to the membrane ans activates the MAPK kinase raf.

(vi) Multiple transcription factors translocate to the nucleus, including NF-kb, NF-AT, AP-1, STAT3 and 5.

See Berridge M.J. *Crit Rev Immunol* (1997) 17:155–178.

T-cell stimulation can be aborted, resulting in a state of anergy (resistance to further stimulation) or apoptosis instead if proliferation and secretion of inflammatory cytokines. THese various responses can be effected (or produced) by altered peptide ligands which differ in their receptor off-rates and in the duration of occupancy. Rabinowitz J.D. et al. *Proc Natl Acad Sci USA* (1996) 93:1401–1404.

PKC is implicated at several steps in these processes. PKC-theta is the first isozyme to translocate. The tight localization at the TCR is only observed with a full agonist peptide. PKC isozymes are involved in mobilization of calcium from intracellular stores, and in opening of calcium channels in the plasma membrane when those stores are depleted. PKC is also implicated in cytoskeletal rearrangements, and in activation of transcription factors such an NF-kb. Mochly-Rosen D. and Kauvar, L.M., *Sem in Immunol* (1999) 12(1): chapter 6.

Each of these processes can be monitored by observing localization of individual PKC isozymes, thus providing markers for sequential and parallel steps in the overall pathway. Disease states can then be analyzed to identify any block and design appropriate countermeasures. Methods to block PKC activity known in the art include antisense and peptides that occupy the catalytic site or the site at which anchoring proteins bind to steer the enzyme to its proper localization. Numerous natural product toxins also target this family of enzymes. Mochly-Rosen D. and Kauvar, L. M., *Adv Pharmacol* (1998) 44:91–145.

EXAMPLE 2

Cystic Fibrosis

The identification of a particular chloride ion channel as the locus to which the vast majority of cases of inherited cystic fibrosis (CF) map has been rightly hailed as a major triumph of genomics research. CF is the most common lethal genetic disease among Caucasians, and identification of the gene has prompted much speculation regarding a gene therapy cure. There are many possible second site revertant strategies being considered as well, however (i.e. intervention elsewhere in the regulatory network to compensate for the primary defect). The actual channel function is regulated by ATP at two sites, coordinated by cAMP dependent kinases (PKA) and by PKC. The role of endogenous and therapeutic small molecule modulators is being investigated. Further, PKC modulates the PKA effects. PKC is also the likely transducer of certain prostaglandins known to influence channel function. Liedtke, C. M. et al. *Am J Physiol* (1998) 275:C1357–64.

The membrane density of the mutant ion channel is reduced by poor stability, making the degradation pathway a potential therapeutic target. An efficient, constitutive internalization of the channel occurs (5% per min), predominantly by clathrin-dependent endocytosis, providing still another target. Thus, compounds which reduce the normal degradation or recycling activity and would therefore normally be considered toxic may be therapeutic in the CF context. Subcellular localization of the channel protein and factors such as PKC that influence it provide assays for such toxins.

Heterozygotes for the CF allele that accounts for 70% of the cases show decreased incidence of childhood asthma. Thus, the same assays used to identify toxins to boost the channel function to treat CF are also useful to identify drugs that decrease it for treatment of asthma.

The invention claimed is:

1. A method to identify an antidote for a toxic compound which method comprises:
    observing an intracellular localization pattern of at least one signal transduction protein in the presence and absence of the toxic compound, said compound supplied at a concentration that is toxic so as to ascertain the intracellular localization pattern under toxic conditions, defined as in the presence of toxic compound, and under normal conditions, defines as in the absence of toxic compound;
    observing the intracellular localization pattern of said at least one signal transduction protein under toxic conditions in the presence of compound that is a candidate for an antidote;
    comparing the intracellular localization pattern under toxic conditions in the presence of the compound that is a candidate for an antidote to the intracellular localization patterns under toxic and normal conditions;
    whereby said compound that is a candidate for an antidote whose presence under toxic conditions restores the intracellular localization pattern to an intracellular localization pattern more closely resembling that under normal conditions is identified as an antidote to the toxic compound;
    wherein said intracellular localization pattern is constructed by determining the presence, absence or level of said signal transduction protein(s) at at least three of nuclear, perinuclear, diffuse cytoplasmic, cytoplasmic fibril-associated and membrane-associated locations.

2. The method of claim 1 wherein the intracellular localization pattern is of at least two signal transduction proteins.

3. The method of claim 2 wherein the intracellular localization pattern is of a multiplicity of signal transduction proteins.

4. A method to identify a compound potentially useful to treat a disease condition in which inhibition of a cellular function ameliorates said disease condition, which method comprises
    observing an intracellular localization pattern of at least one signal transduction protein in the presence and the absence of a candidate compound;
    observing the intracellular localization pattern of said signal transduction protein in the presence of an inhibitor known to inhibit said cellular function;
    comparing the observed intracellular localization patterns,
    whereby said candidate compound is identified as potentially useful in treating the disease condition if the intracellular localization pattern observed in the presence of the candidate compound more closely resembles that observed in the presence of a known inhibitor than does the intracellular localization pattern in the absence of the candidate compound;
    wherein said intracellular localization pattern is constructed by determining the presence, absence or level of said signal transduction protein(s) at at least three of nuclear, perinuclear, diffuse cytoplasmic, cytoplasmic fibril-associated and membrane-associated locations.

5. A method to identify a therapeutic protocol potentially effective for the treatment of a disease condition which method comprises
    providing an intracellular localization profile of a multiplicity of signal transduction proteins characteristic of said disease condition;
    providing an intracellular localization profile of a multiplicity of signal transduction proteins characteristic of normal cells;
    administering said protocol to cells or tissues exhibiting said profile characteristic of the disease condition; and
    observing the effect of said therapeutic protocol on said profile, whereby a therapeutic protocol which results in conversion of said profile to a profile more closely resembling that of normal cells identifies said protocol as a potentially effective protocol;
    wherein said profile is constructed by determining the presence, absence or level of said signal transduction protein(s) at at least three of nuclear, perinuclear, diffuse cytoplasmic, cytoplasmic fibril-associated and membrane-associated locations.

6. The method of claim 4, wherein the intracellular localization pattern is of at least two signal transduction proteins.

7. The method of claim 6, wherein the intracellular localization pattern is of a multiplicity of signal transduction proteins.

8. The method of claim 1, wherein said observing is by microscopy.

9. The method of claim 4, wherein said observing is by microscopy.

10. The method of claim 5, wherein said observing is by microscopy.

11. The method of claim 1, wherein the localization pattern is observed in fixed cells.

12. The method of claim 4, wherein the localization pattern is observed in fixed cells.

13. The method of claim 5, wherein the localization profile is observed in fixed cells.

* * * * *